(12) United States Patent
Hersh et al.

(10) Patent No.: US 8,690,786 B2
(45) Date of Patent: Apr. 8, 2014

(54) SYSTEM AND METHOD FOR A NON-INVASIVE BLOOD PRESSURE MONITOR

(75) Inventors: Lawrence Hersh, Tampa, FL (US); Richard Medero, Tampa, FL (US); Sai Kolluri, Tampa, FL (US); William Roberts, Jacksonville, FL (US)

(73) Assignee: General Electric Company, Schenectady, NY (US)

( * ) Notice: Subject to any disclaimer, the term of this patent is extended or adjusted under 35 U.S.C. 154(b) by 975 days.

(21) Appl. No.: 12/143,902

(22) Filed: Jun. 23, 2008

(65) Prior Publication Data

US 2009/0318828 A1    Dec. 24, 2009

(51) Int. Cl.
*A61B 5/02* (2006.01)
*A61B 8/00* (2006.01)

(52) U.S. Cl.
USPC .......................................... 600/485; 600/450

(58) Field of Classification Search
None
See application file for complete search history.

(56) References Cited

U.S. PATENT DOCUMENTS

| | | | | |
|---|---|---|---|---|
| 4,754,761 A | * | 7/1988 | Ramsey et al. | 600/496 |
| 2002/0062086 A1 | * | 5/2002 | Miele et al. | 600/483 |
| 2005/0171443 A1 | * | 8/2005 | Gorenberg et al. | 600/490 |

* cited by examiner

*Primary Examiner* — Jim Ketter
*Assistant Examiner* — Reza Ghafoorian
(74) *Attorney, Agent, or Firm* — Andrus Intellectual Property Law, LLP

(57) ABSTRACT

A non-invasive blood pressure system is disclosed herein. The non-invasive blood pressure system includes a pressure transducer configured to obtain pressure data comprising a transient baseline effects component. The non-invasive blood pressure system also includes a processor adapted to receive the pressure data from the pressure transducer. The processor is configured to generate a transient baseline effects model, and to implement the transient baseline effects model to at least partially remove the transient baseline effects component of the pressure data. The removal of the transient baseline effects component from the pressure data eliminates a potential source of error and thereby enables a more accurate blood pressure estimate.

18 Claims, 4 Drawing Sheets

SYSTEM AND METHOD FOR A NON-INVASIVE BLOOD PRESSURE MONITOR

BACKGROUND OF THE INVENTION

The subject matter disclosed herein relates to a system and method for a non-invasive blood pressure monitor. More specifically, the subject matter disclosed herein relates to a system and method for a non-invasive blood pressure monitor that is configured to more accurately estimate one or more blood pressure parameters.

Non-invasive blood pressure (NIBP) monitors typically inflate a pressure cuff above the patient's systolic pressure and measure very small amplitude pressure oscillations within the cuff as the cuff is deflated either in steps or continuously. The pressure oscillations in the cuff are due to volume oscillations resulting from the heart beating and pumping blood through the arterial system. The size of the cuff pressure oscillations changes as the cuff pressure itself changes. The data set which describes the cuff oscillation size as a function of the cuff pressure is commonly known as the oscillometric envelope. The resulting oscillometric envelope obtained from the cuff pressure data is used to determine the patient's blood pressure. The cuff pressure corresponding to the maximum oscillation amplitude is typically taken as the mean arterial pressure (MAP). Systolic and Diastolic pressures are computed by finding the cuff pressure levels at which a fixed ratio of the maximum oscillation amplitude occurs. Some NIBP monitors also use details in the shape of the oscillometric envelope to compute the Systolic and Diastolic pressures.

The cuff pressure data can, in some cases, contain various types of artifacts that may hinder the ability of the NIBP device to estimate blood pressure values accurately. Two primary classes of artifacts are patient motion and transient baseline effects. Conventional NIBP techniques are not capable of handling these artifact problems effectively and this can often introduce imprecision into the blood pressure estimates, and may also result in longer determination times which can be uncomfortable to the patient. Transient baseline effects are well known to those skilled in the art, and may include such phenomena as the heating and cooling of the air within the cuff, the visco-elastic effects of the cuff material which influence the time needed to reach pressure-volume equilibrium, and physiological changes in fluid and tissue volume under the cuff.

BRIEF DESCRIPTION OF THE INVENTION

The above-mentioned shortcomings, disadvantages and problems are addressed herein which will be understood by reading and understanding the following specification.

In an embodiment, a non-invasive blood pressure system includes a pressure transducer configured to obtain pressure data comprising a transient baseline effects component. The non-invasive blood pressure system also includes a processor adapted to receive the pressure data from the pressure transducer. The processor is configured to generate a transient baseline effects model, and to implement the transient baseline effects model to at least partially remove the transient baseline effects component of the pressure data. The removal of the transient baseline effects component from the pressure data eliminates a potential source of error and thereby enables a more accurate blood pressure estimate.

In another embodiment, a non-invasive blood pressure system includes an inflatable cuff, and a pressure transducer pneumatically coupled with the inflatable cuff. The pressure transducer is configured to obtain pressure data comprising an oscillatory component and a transient baseline effects component. The non-invasive blood pressure system also includes a processor adapted to receive the pressure data from the pressure transducer. The processor is configured to generate a non-linear transient baseline effects model, and to implement the non-linear transient baseline effects model to at least partially remove the transient baseline effects component of the pressure data such that substantially only the oscillatory component remains. The processor is further configured to estimate a blood pressure parameter based on the oscillatory component of the pressure data. The non-invasive blood pressure system also includes a display configured to visually convey the estimated blood pressure parameter. The removal of the transient baseline effects component from the pressure data eliminates a potential source of error and thereby improves the accuracy of the estimated blood pressure parameter.

In another embodiment, a method includes implementing a pressure transducer and an inflatable cuff to obtain pressure data comprising an oscillatory component and a transient baseline effects component, and implementing a processor to generate a non-linear transient baseline effects model based on a plurality of data points acquired from a plot of the pressure data. The method also includes implementing the transient baseline effects model to remove at least a portion of the transient baseline effects component from the pressure data such that substantially only the oscillatory component remains, and implementing the oscillatory component of the pressure data to estimate a blood pressure parameter. The removal of the transient baseline effects component from the pressure data eliminates a potential source of error and thereby enables a more accurate estimate of the blood pressure parameter.

Various other features, objects, and advantages of the invention will be made apparent to those skilled in the art from the accompanying drawings and detailed description thereof.

DETAILED DESCRIPTION OF THE INVENTION

In the following detailed description, reference is made to the accompanying drawings that form a part hereof, and in which is shown by way of illustration specific embodiments that may be practiced. These embodiments are described in sufficient detail to enable those skilled in the art to practice the embodiments, and it is to be understood that other embodiments may be utilized and that logical, mechanical, electrical and other changes may be made without departing from the scope of the embodiments. The following detailed description is, therefore, not to be taken as limiting the scope of the invention.

Figure 1:
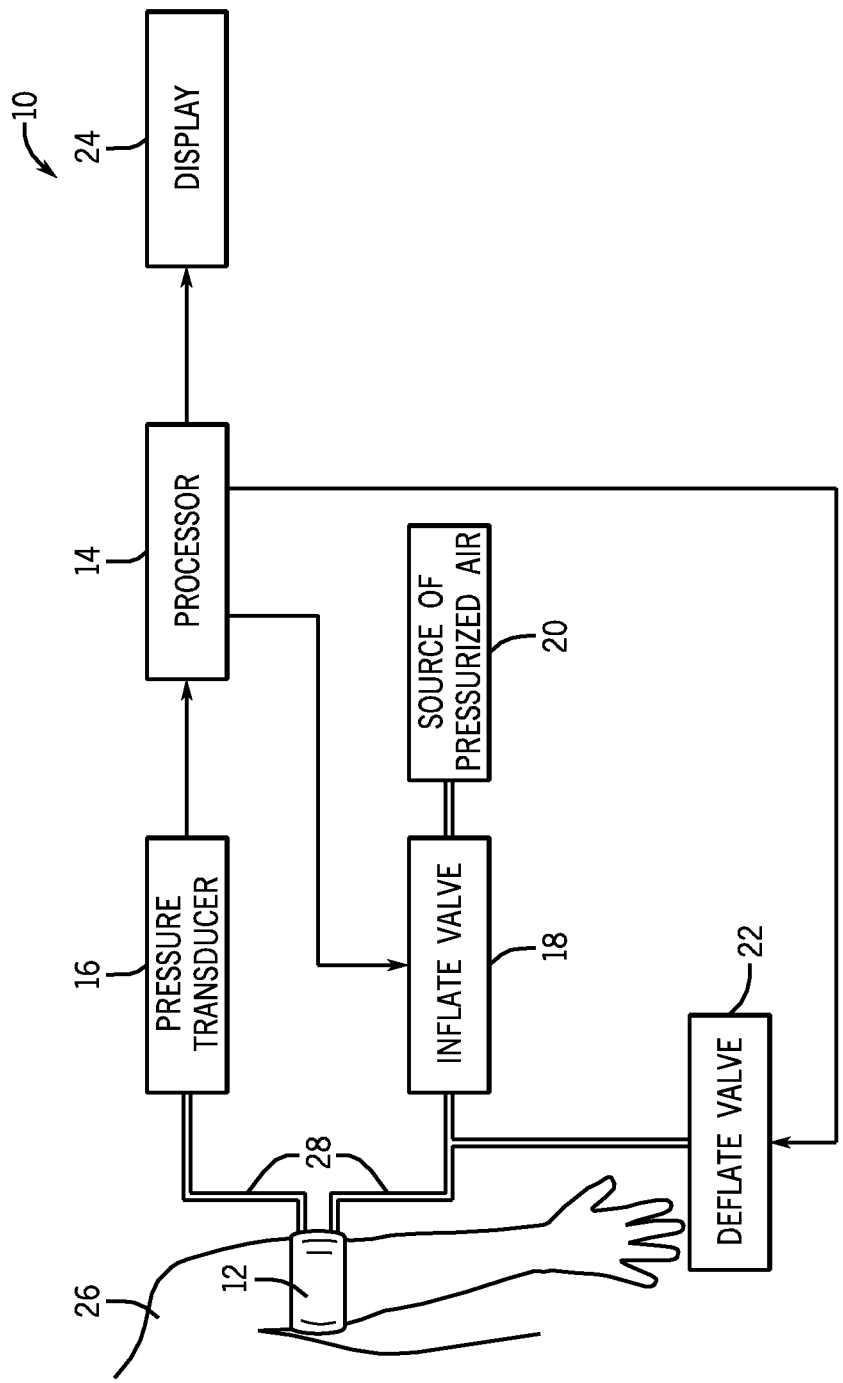
FIG. 1 is a schematic representation of a non-invasive blood pressure system in accordance with an embodiment.

Referring to FIG. 1, a non-invasive blood pressure (NIBP) system 10 is shown in accordance with an embodiment. The NIBP system 10 includes an inflatable cuff 12, a processor 14, a pressure transducer 16, an inflation valve 18, a source of pressurized air 20, a deflation valve 22 and a display 24. In the embodiment depicted, the inflatable cuff 12 is wrapped around the patient's upper arm 26, however other locations (e.g., forearm, wrist, finger) and other limbs could also be used. The inflatable cuff 12 is pneumatically coupled with the pressure transducer 16, the inflation valve 18 and the deflation valve 22 via a flexible tube 28. The processor 14 is electronically coupled with the pressure transducer 16, the inflation valve 18, the deflation valve 22 and the display 24.

The processor 14 is configured to coordinate the operation of valves 18, 22 in a manner adapted to regulate cuff 12 inflation and deflation. More precisely, the processor 14 can selectively open the inflation valve 18 in order to allow the source of pressurized air 20 to inflate the cuff 12, and selectively open the deflation valve 22 to release the pressurized air and thereby deflate the cuff 12. The pressure transducer 16 is configured to sense or identify pressure pulses referred to hereinafter as NIBP pulses at the portion of the patient's arm 26 to which the cuff 12 is attached. Thereafter, the pressure transducer 16 can transmit pressure data comprising data pertaining to the NIBP pulses to the processor 14.

Figure 2:
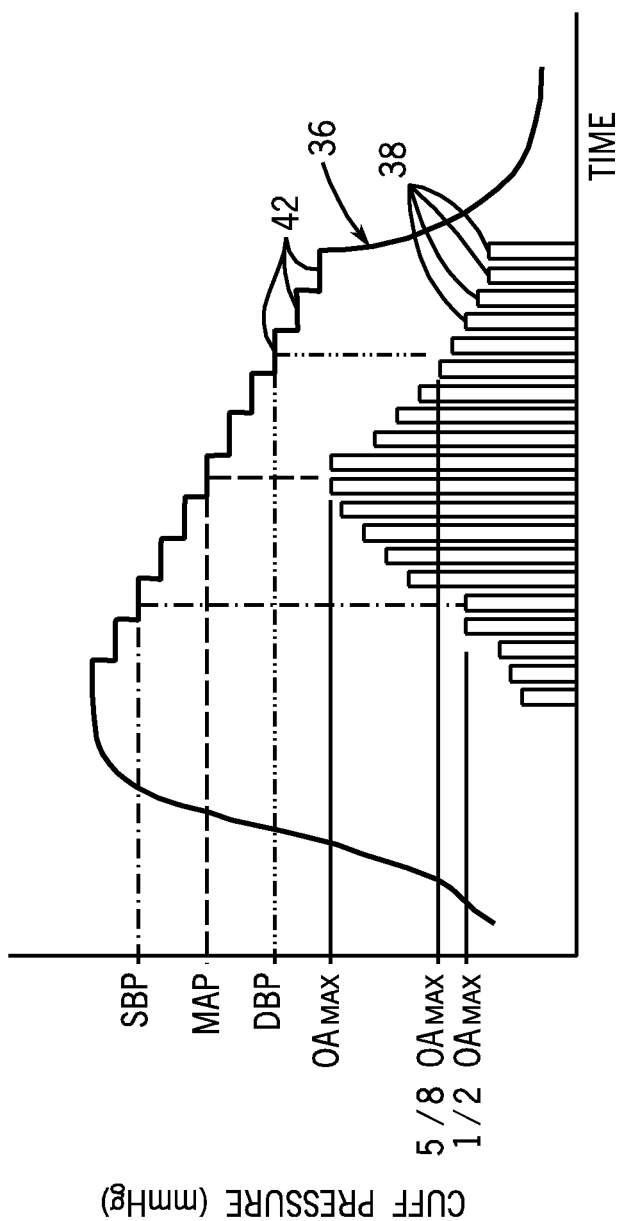
FIG. 2 is a graph of cuff pressure versus time illustrating a method for estimating a blood pressure parameter.

The processor 14 is configured to estimate a blood pressure parameter such as mean arterial pressure (MAP), systolic blood pressure (SBP), and/or diastolic blood pressure (DBP) based on the pressure data from the pressure transducer 16. The processor 14 is also configured to transmit the estimated MAP, SBP and/or DBP values to the display 24. The display 24 is configured to visually convey the estimated MAP, SBP and/or DBP values. With reference to FIGS. 1 and 2, an exemplary process of estimating MAP, SBP and DBP will be described in accordance with one embodiment.

The exemplary process of estimating MAP, SBP and/or DBP is performed by increasing and decreasing the pressure of the cuff 12 in the manner illustrated by the cuff pressure curve 36 of FIG. 2, and generally simultaneously measuring a series of NIBP pulses 38. This process is initiated by inflating the cuff 12 to a supra-systolic pressure level. As is known in the art, at supra-systolic cuff pressure blood is completely occluded or obstructed from flowing through the artery under the cuff 12, systolic pressure is the cuff pressure level at which blood just begins flowing through the artery under the cuff 12, and diastolic pressure is the cuff pressure level at which blood flow through the artery under the cuff 12 is unobstructed. After cuff 12 pressure is increased to a supra-systolic pressure level, the cuff 12 is deflated (via valve 22) in a controlled manner adapted to produce a series of decreasing pressure level steps 42. It should be appreciated that while the exemplary embodiment has been described and depicted as including a stepwise cuff pressure reduction, other embodiments may alternatively implement a generally continuous cuff pressure reduction. Additional possible embodiments include other cuff inflation and deflation patterns.

After the cuff 12 reaches systolic pressure, the pressure level measured by the pressure transducer 16 oscillates due to the force generated by the entry of blood into the artery under the cuff 12. The term "oscillation" refers to a measurable pressure level oscillation produced by this change in volume. Two consecutive oscillations are generally measured at each cuff pressure level step to guarantee consistency in the measurement of the pulse properties for that step and thereby reject artifact. As shown in FIG. 2, MAP is identifiable as the cuff pressure level at which oscillation amplitude is maximum ($OA_{max}$). SBP is identifiable as the cuff pressure level at which oscillation amplitude is approximately equal to ($0.5 * (OA_{max})$), and DBP is identifiable as the cuff pressure level at which oscillation amplitude is approximately equal to ($0.625 * (OA_{max})$). The actual fractions of $OA_{max}$ used to find systolic and diastolic estimates depends upon the signal processing implemented and can be further influenced by the experience of those skilled in the art of oscillometry.

It should be appreciated that transient baseline effects can introduce imprecision into the blood pressure measurement. More precisely, transient baseline effects can vary the pressure level reading acquired by the pressure transducer 16 at each step 42, and can also complicate the process of detecting and measuring pulse property details. This pressure level variation correspondingly varies the oscillation amplitude measurements and the resultant MAP, SBP and DBP estimates. In a non-limiting manner, transient baseline effects may include any effect caused by the heating and cooling of the air within the cuff, the visco-elastic properties of the cuff material, and any physiological changes in fluid volume or tissue response under the cuff. Transient baseline effects are well known to those skilled in the art and therefore will not be described in further detail.

Figure 3:
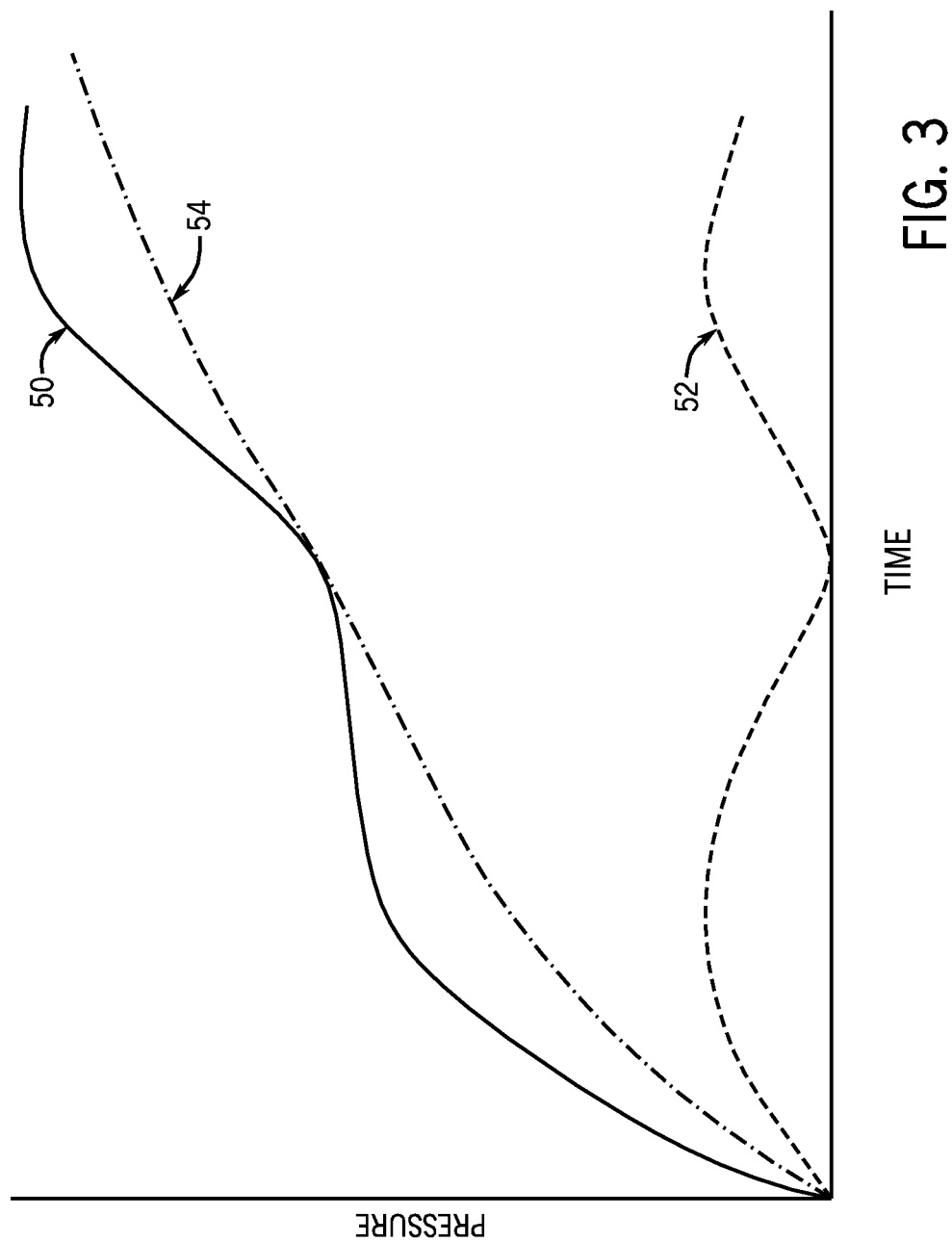
FIG. 3 is an exemplary plot of pressure data comprising an oscillatory component and a transient baseline effects component.

Referring to FIG. 3, a plot 50 represents filtered pressure data acquired from the pressure transducer 16 (shown in FIG. 1) during one of the steps 42 (shown in FIG. 2) of the pressure curve 36 (shown in FIG. 2). Filtering is implemented to more clearly identify the constituent parts of the pressure data, and it should be appreciated that there are a variety of filtering methods that may be implemented for this purpose. According to one embodiment, the pressure data may be filtered with an amplified band-pass filter. The depicted portion of the plot 50 comprises an oscillatory component 52 attributable to the patient's cardiac activity, and a transient baseline effects component 54. While shown and described hereinafter as producing a steadily increasing pressure level, the transient baseline effects component 54 may alternatively cause the pressure level to decrease during some of the steps 42 of a blood pressure determination.

It should be appreciated that the transient baseline effects component 54 of the plot 50 is responsible for introducing imprecision into the MAP, SBP and DBP estimates since it may cause uncertainty in the estimation of the pulse amplitude and corrupt the oscillometric envelope data. Accordingly, as will be described in detail hereinafter, the transient baseline effects component 54 may be modeled or otherwise approximated and thereafter subtracted from the plot 50 such that substantially only the oscillatory component 52 remains. Thereafter, the oscillatory component 52 may be implemented to estimate MAP, SBP and DBP in a manner that minimizes the imprecision associated with the transient baseline effects.

The transient baseline effects component 54 of the plot 50 can be modeled or estimated in a variety of different ways. The following will describe an embodiment wherein the processor 14 (shown in FIG. 1) generates an exponential transient baseline effects model 56 (shown in FIG. 4) as an estimate of the transient baseline effects component 54 of the plot 50. It should, however, be appreciated that the transient baseline effects component 54 may alternatively be modeled based on other types of equations such as, for example, a polynomial based model.

Figure 4:
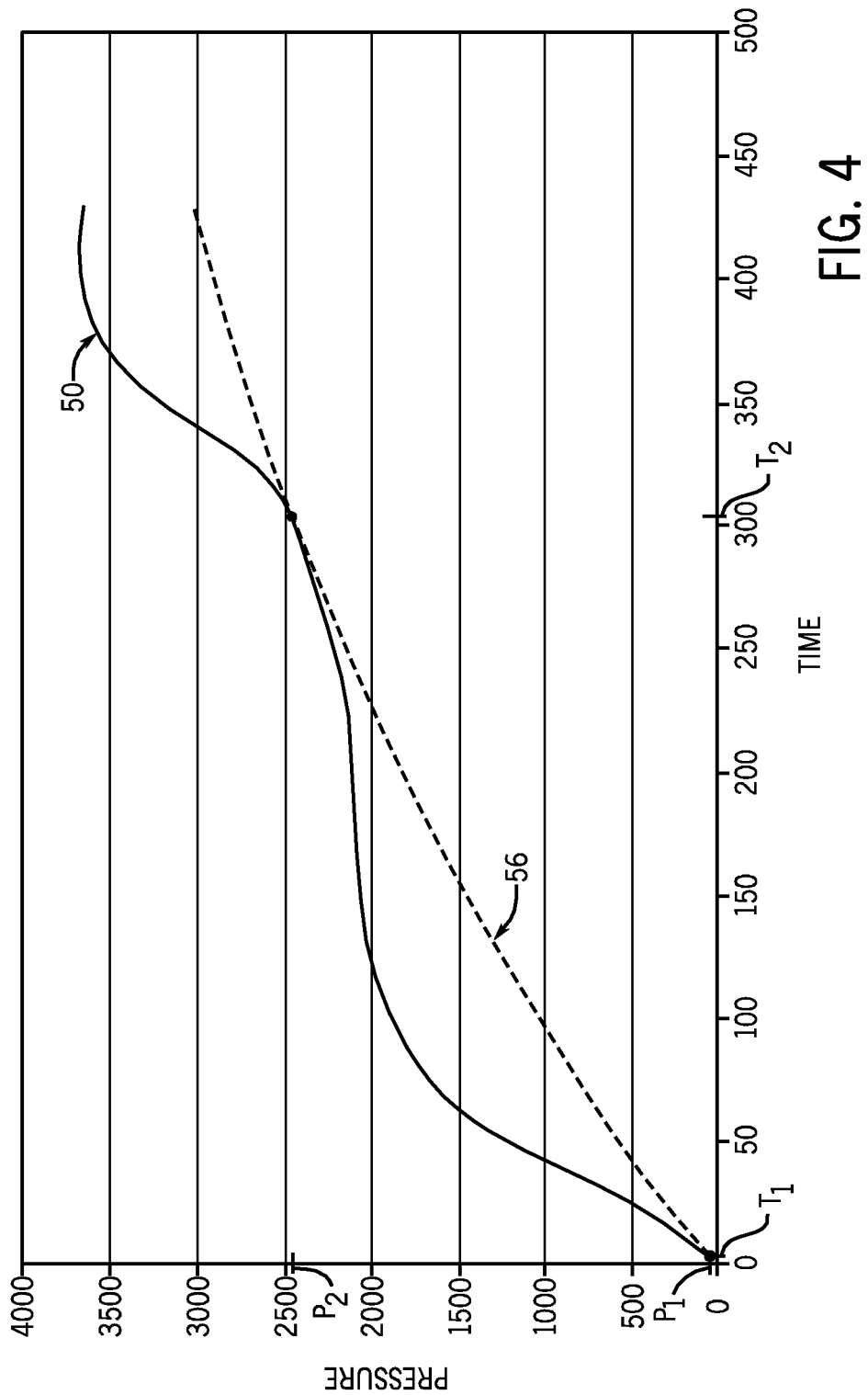
FIG. 4 is the plot of pressure data from FIG. 3 and a transient baseline effects model in accordance with an embodiment.

Referring to FIG. 4, the transient baseline effects model 56 is initially established by implementing the processor 14 (shown in FIG. 1) to identify points ($t_1, p_1$) and ($t_2, p_2$) that are common to both the plot 50 and the transient baseline effects model 56. According to one embodiment, the points ($t_1, p_1$) and ($t_2, p_2$) of the transient baseline effects model 56 are defined as consecutive relative minimum values of the plot 50. The selection of relative minimum values is convenient in that they are generally easy to identify, however, it should be appreciated that any other consistent phase point (e.g., relative maximum values) of the plot 50 may alternatively be implemented.

After identifying the points $(t_1, p_1)$ and $(t_2, p_2)$, the remainder of the transient baseline effects model 56 can be solved by the processor 14 (shown in FIG. 1) using the following exponential equation: $P_t = Ae^{-(t-t_1)/\tau} + B$. The variable $P_t$ represents the pressure of the transient baseline effects model 56 at time t, the variable A represents the magnitude of the change of the transient baseline effects model 56, the variable B represents the equilibrium or steady state pressure of the transient baseline effects model 56, and the variable $\tau$ is a time constant. Experimentation based on a variety of different transient baseline effects models has revealed that the time constant $\tau$ is generally approximately equal to one second. Alternate embodiments may generate a transient baseline effects model based on any line or curve incorporating the points $(t_1, p_1)$ and $(t_2, p_2)$.

The exponential equation $P_t = Ae^{-(t-t_1)/\tau} + B$ can be solved by deriving two equations in the following manner. The first derived equation is obtained by evaluating the exponential equation at time $t_1$ such that $t=t_1$ and $P_t = p_1$, and solving for B. The first derived equation becomes: $B = p_1 - A$. The second derived equation is obtained by evaluating the exponential equation at time $t_2$ such that $t=t_2$ and $P_t = p_2$, replacing the variable B with the quantity $(p_1 - A)$ per the first derived equation, and solving for A. The second derived equation becomes $A = (p_1 - p_2)/(1 - e^{-(t_2-t_1)/\tau})$. The two derived equations can be algebraically solved by setting the time constant $\tau$ equal to one second and inputting relative minimum values from the plot 50 for points $(t_1, p_1)$ and $(t_2, p_2)$. This yields two equations and two unknowns such that the variables A and B can be solved. Alternatively, the variables A, B and $\tau$ can all be solved for by obtaining a third relative minimum point $(t_3, p_3)$ from the plot 50, and evaluating the exponential equation at time $t_3$ to derive a third equation, such that there are three equations and three unknowns.

After solving for or otherwise obtaining values for A, B and $\tau$, the exponential equation $P_t = Ae^{-(t-t_1)/\tau} + B$ is solvable to completely define the transient baseline effects model 56. Thereafter, the complete transient baseline effects model 56 or any portion thereof can be removed (e.g., subtracted) from the pressure data of plot 50 in order to eliminate or at least minimize the imprecision introduced by the transient baseline effects. It should be appreciated that the elimination or minimization of the transient baseline effects imprecision in the manner described provides a more accurate estimate of MAP, SBP, and DBP.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

We claim:

1. A non-invasive blood pressure measuring system comprising: a single pressure transducer configured to obtain pressure data at each of a plurality of decreasing pressure steps, said pressure data at each decreasing pressure step including a transient baseline effects component; and A processor adapted to receive the pressure data obtained by the single pressure transducer at each of the plurality of decreasing pressure steps, said processor being configured to generate a transient baseline effects model at each pressure step based on the pressure data obtained by the single pressure transducer, said processor further being configured to implement the transient baseline effects model to at least partially remove the transient baseline effects component from the pressure data received from the single pressure transducer at each one of the plurality of decreasing pressure steps, wherein the processor estimates a blood pressure parameter from the pressure data, obtained by the single pressure transducer at each one of the plurality of decreasing pressure steps after removal of the transient baseline effects component;

wherein the removal of the transient baseline effects component from the pressure data obtained at each of the plurality of decreasing pressure steps eliminates a potential source of error and thereby enables a more accurate blood pressure estimate.

2. The non-invasive blood pressure system of claim 1, wherein said processor is configured to generate a non-linear transient baseline effects model.

3. The non-invasive blood pressure system of claim 1, wherein said processor is configured to generate the transient baseline effects model based on a plurality of data points acquired from a plot of the pressure data obtained at each one of the plurality of decreasing pressure steps.

4. The non-invasive blood pressure system of claim 1, wherein said processor is configured to generate the transient baseline effects model based on a plurality of consecutive phase points acquired from a plot of the pressure data obtained at each one of the plurality of decreasing pressure steps.

5. The non-invasive blood pressure system of claim 1, further comprising an inflatable cuff electronically coupled with the processor and pneumatically coupled with the pressure transducer.

6. The non-invasive blood pressure system of claim 5, wherein the processor is configured to regulate the inflation and/or deflation of the inflatable cuff in a generally stepwise manner between the plurality of decreasing pressure steps.

7. A non-invasive blood pressure system comprising:
an inflatable cuff inflatable and deflatable between a plurality of decreasing pressure steps;
a single pressure transducer pneumatically coupled with the inflatable cuff, said single pressure transducer configured to obtain pressure data at each one of the plurality of decreasing pressure steps including an oscillatory component and a transient baseline effects component;
a processor adapted to receive the pressure data obtained by the single pressure transducer at each one of the plurality of decreasing pressure steps, said processor being configured to generate a non-linear transient baseline effects model based on the pressure data obtained at each one of the plurality of decreasing pressure steps, said processor further being configured to implement the non-lineal transient baseline effects model to at least potentially remove the transient baseline effects component from the pressure data received from the single pressure transducer at each one of the plurality of decreasing pressure steps, such that only the oscillatory component remains, said processor further being configured to estimate a blood pressure parameter from the oscillatory component of the pressure data obtained by the single pressure transducer at each one of the plurality of decreasing pressure steps; and a display configured to visually convey the estimated blood pressure parameter; wherein the removal of the transient baseline effects component from the pressure data eliminates a potential source of error and thereby improves the accuracy of the estimated blood pressure parameter.

8. The non-invasive blood pressure system of claim 7, wherein said processor is configured to generate the transient baseline effects model based on a plurality of data points acquired from a plot of the pressure data obtained at each of the plurality of decreasing pressure steps.

9. The non-invasive blood pressure system of claim 8, wherein said processor is configured to generate the transient baseline effects model based on a plurality of consecutive phase points acquired from a plot of the pressure data obtained at each one of plurality of decreasing pressure steps.

10. The non-invasive blood pressure system of claim 7, wherein the processor is configured to regulate the inflation and/or deflation of the inflatable cuff in a generally stepwise manner between the plurality of decreasing pressure steps.

11. The non-invasive blood pressure system of claim 1, wherein said processor is configured to generate a linear transient baseline effects model.

12. The non-invasive blood pressure system of claim 1, wherein said processor is configured to generate an exponential transient baseline effects model.

13. The non-invasive blood pressure system of claim 5, wherein the processor is configured to regulate the inflation and/or deflation of the inflatable cuff in a generally continuous manner.

14. The non-invasive blood pressure system of claim 7, wherein said processor is configured to generate an exponential transient baseline effects model.

15. The non-invasive blood pressure system of claim 7, wherein the processor is configured to regulate the inflation and/or deflation of the inflatable cuff in a generally continuous manner.

16. A method comprising:

implementing a single pressure transducer and an inflatable cuff to obtain pressure data comprising an oscillatory component and a transient baseline effects component at a plurality of decreasing pressure steps;

implementing a processor to generate a non-linear transient baseline effects model from a plurality of data points acquired from a plot of the pressure data from the single pressure transducer at each one of the plurality of decreasing pressure steps;

implementing the transient baseline effects model at each one of the plurality of decreasing pressure steps to remove at least a portion of the transient baseline effects component from the pressure data received from the single pressure transducer; and implementing the remaining oscillatory component of the pressure data obtained by the single pressure transducer at each one of the decreasing pressure steps to estimate a blood pressure parameter;

wherein the removal of the transient baseline effects component from the pressure data eliminates a potential source of error and thereby enables a more accurate estimate of the blood pressure parameter.

17. The method of claim 16, further comprising filtering the pressure data before generating the non-linear transient baseline effects model.

18. The method of claim 16, wherein said implementing a processor to generate a non-linear transient baseline effects model includes generating an exponential transient baseline effects model using the equation $P_t = Ae^{-(t-t_1)/\tau} + B$.

* * * * *